US012805742B2

(12) United States Patent
Satoh et al.

(10) Patent No.: US 12,805,742 B2
(45) Date of Patent: Nov. 24, 2026

(54) MAGNETIC RESONANCE IMAGING APPARATUS, IMAGE PROCESSOR, AND IMAGE PROCESSING METHOD

(71) Applicant: FUJIFILM Healthcare Corporation, Kashiwa (JP)

(72) Inventors: Ryota Satoh, Chiba (JP); Toru Shirai, Chiba (JP); Hisaaki Ochi, Chiba (JP); Yoshihiro Iwata, Chiba (JP); Yoshitaka Bito, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 240 days.

(21) Appl. No.: 18/118,798

(22) Filed: Mar. 8, 2023

(65) Prior Publication Data

US 2023/0309848 A1 Oct. 5, 2023

(30) Foreign Application Priority Data

Mar. 31, 2022 (JP) ................................ 2022-060537

(51) Int. Cl.
*A61B 5/055* (2006.01)

(52) U.S. Cl.
CPC .......... *A61B 5/055* (2013.01); *A61B 2576/00* (2013.01); *G06T 2207/10088* (2013.01)

(58) Field of Classification Search
CPC ..... A61B 5/0071; A61B 5/0077; A61B 5/418; A61B 5/4878; A61B 5/7267;
(Continued)

(56) References Cited

U.S. PATENT DOCUMENTS 6,430,430 B1 * 8/2002 Gosche .................. G06T 7/155 128/923
2011/0033099 A1 * 2/2011 Kadomura ............. G06T 7/143 382/131
(Continued)

FOREIGN PATENT DOCUMENTS

JP 2006-502751 A 1/2006
JP 2020-08695 A 2/2020
(Continued)

OTHER PUBLICATIONS

Official action dated Feb. 7, 2025 from the European Patent Office, in connection with European Patent Application No. 23 161 628.5.
(Continued)

*Primary Examiner* — Bo Joseph Peng

(57) ABSTRACT

Provided is a means that uses a two-dimensional image to distinguish a small region from other regions within the image and to highlight the small region. On the basis of the two-dimensional image where an organ such as blood vessels or a lesion such as microbleeds (collectively referred to as a designated region) is visualized, the designated region is discriminated from other regions, using a shape feature of the designated region and spatial feature of the space where the designated region exists. The spatial feature includes at least one of the followings; a spatial tissue distribution (presence probability for each tissue) of the designated region, and a spatial brightness distribution of pixel values of the designated region.

15 Claims, 16 Drawing Sheets

(58) Field of Classification Search
CPC . A61B 5/7275; A61B 5/7425; A61B 1/00006; A61B 1/000094; A61B 1/000096; A61B 1/00167; A61B 1/00186; A61B 1/042; A61B 1/043; A61B 1/0638; A61B 1/07; A61B 1/3132; A61B 5/0035; A61B 5/0084; A61B 5/742; G06T 11/60; G06T 2210/41; G06T 7/0012; G16H 30/40; G16H 50/30; G16H 10/60; G16H 20/30; G16H 20/40; G16H 30/20; G16H 40/67; G16H 50/20; G16H 50/70
See application file for complete search history.

(56) References Cited

U.S. PATENT DOCUMENTS

| | | | | |
|---|---|---|---|---|
| 2013/0136322 | A1* | 5/2013 | Zhan | G06T 7/73 382/128 |
| 2014/0122515 | A1 | 5/2014 | Lee et al. | |
| 2014/0334708 | A1* | 11/2014 | Sakata | A61B 6/5288 382/131 |
| 2015/0065803 | A1* | 3/2015 | Douglas | G06T 7/143 600/200 |
| 2019/0139223 | A1* | 5/2019 | Nie | G06V 10/25 |
| 2019/0378621 | A1* | 12/2019 | Ellison | G06F 3/011 |
| 2021/0049756 | A1* | 2/2021 | He | G06N 3/04 |
| 2021/0158511 | A1* | 5/2021 | Guo | G06T 7/0012 |
| 2021/0256691 | A1* | 8/2021 | Sepehrband | G06T 7/11 |
| 2021/0401407 | A1* | 12/2021 | Yang | A61B 8/0841 |
| 2022/0087562 | A1 | 3/2022 | Ferris et al. | |
| 2023/0298170 | A1* | 9/2023 | Brickman | G06T 7/13 382/131 |

FOREIGN PATENT DOCUMENTS

| | | | |
|---|---|---|---|
| JP | 6775944 | B2 | 10/2020 |
| JP | 2021-183017 | A | 12/2021 |
| JP | 2022-018097 | A | 1/2022 |
| WO | WO2020/050272 | A1 | 3/2020 |

OTHER PUBLICATIONS

Hugo J. Kuijf et al., "Powerful Detection of Cerebral Microbleeds on 7.0T MR Phase Gradient Magnitude Images Using the Radial Symmetry Transform", Proc. ISRM 1066 (2012).

Hangfan Liu et al., "Cerebral Microbleed Detection Via Fourier Descriptor with Dual Domain Distribution Modeling", IEEE 17th Int'l Symp Biomedical Imaging Workshops (2020).

European search report dated Aug. 14, 2023 in connection with European Patent Application No. 23 16 1628.

Chesebro, Anthony G. et al., "Automated detection of cerebral microbleeds on T2*-weighted MRI", Scientific Reports, vol. 11, No. 1 (Feb. 17, 2021).

Roy, Snehashis et al., "Cerebral Microbleed Segmentation from Susceptibility Weighted Images", Proc SPIE, vol. 9413, pp. 94131E-94131E (Mar. 20, 2015).

Liu, Saifeng et al., "Cerebral microbleed detection using Susceptibility Weighted Imaging and deep learning", NeuroImage, vol. 198, pp. 271-282 (Sep. 1, 2019).

Kuijf, Hugo J. et al., "Semi-Automated Detection of Cerebral Microbleeds on 3.0 T MR Images", PLOS ONE, vol. 8, No. 6, p. e66610 (Jun. 21, 2013).

Sundaresan Vaanathi et al., "Automated Detection of Cerebral Microbleeds on MR images using Knowledge Distillation Framework", medRxiv, pp. 1-41 (Nov. 16, 2021).

Japanese official action dated Feb. 18, 2025 from the Japanese Patent Office, in connection with Japanese Patent Application No. 2022-060537.

Jun. 10, 2025 Japanese official action (and English translation thereof) in connection with Japanese Patent Application No. 2022-060537.

Vaanathi Sundaresan, et al., "Automated Detection of Candidate Subjects With Cerebral Microbleeds Using Machine Learning", Front Neuroinform, 20:15:777828 (2022).

Aug. 12, 2026 Chinese official action (and machine translation in English thereof) in connection with Chinese Patent Application No. 2022111469756.

* cited by examiner

MAGNETIC RESONANCE IMAGING APPARATUS, IMAGE PROCESSOR, AND IMAGE PROCESSING METHOD

BACKGROUND OF THE INVENTION

Technical Field

The present invention relates to a magnetic resonance imaging (MRI) apparatus, and more particularly, to a technique for highlighting a designated region in an MR image of an examination target.

Description of the Related Art

MRI is a technique for processing nuclear magnetic resonance signals generated from respective tissues of an examination target to create an image with different tissue contrasts, and this technique is widely utilized for image diagnosis support. The MRI allows obtainment of various images with different tissue contrasts by adjusting conditions (imaging conditions) under which nuclear magnetic resonance signals are generated. Furthermore, depending on examination purposes and objects, it is possible to acquire one or more types of images, such as T2* weighted images, T1 weighted images, proton density weighted images, and diffusion weighted images (susceptibility weighted images).

Among such various contrasted images, the T2* images emphasize differences in the transverse relaxation time TE (apparent transverse relaxation time T2*) of tissues, by extending the echo time TE. Thus, the T2* images are useful for diagnosing a lesion with a high susceptibility effect (e.g., hemorrhage) in brain images examples. Accordingly, many examination protocols include T2* weighted imaging as one of standard imaging types.

In MRI, according to a method for applying a gradient magnetic field that is applied when generating nuclear magnetic resonance signals, multi-slice 2D images and 3D images can be acquired. Usually, blood vessels travel linearly in the tissue, and when an attempt is made to discriminate between blood vessels and microbleeds (microhemorrhage or minor leak) in an MR image, the blood vessel is difficult to be identified in a 2D (two-dimensional) image, because the blood vessel is depicted as a small dot-like image, except for the blood vessel that travels along the cross section. It is particularly difficult to distinguish between normal blood vessels and microbleeds, and conventionally, algorithms for distinguishing between the normal blood vessels and the microbleeds are based on a 3D (three-dimensional) image.

For example, the specification of JP Patent No. 6775944 (hereinafter, referred to as Patent Literature 1) discloses that a projection process is performed on three-dimensional image data of a brain in a range from the brain surface to a predetermined depth, thereby acquiring a projection image that visualizes MB (microbleeds) or calcification generated in the brain. Furthermore, as a technique for discriminating the microbleeds, JP-A-2020-18695 (hereinafter, referred to as Patent Literature 2) discloses a technique for distinguishing between blood vessels and microbleeds, from a plurality of images obtained at different timings, utilizing that signals of venous blood and microbleeds have the same influence of magnetic susceptibility, but have different influence on phase caused by a blood flow.

SUMMARY OF THE INVENTION

Technical Problem

Although 3D images are suitable for grasping a three-dimensional structure, there are problems as the following; for example, the time for imaging is generally longer than that of 2D images, and the images are susceptible to body motion. Furthermore, in the technique described in Patent Literature 1, although the projecting process allows displaying of an image where calcification or MB can be easily distinguished, a doctor or an examiner is required to view the image to determine whether or not the microbleeds are occurring, and an algorithm for this determination is not provided. In the technique described in Patent Literature 2, there are acquired echoes (nuclear magnetic resonance signals) for obtaining a plurality of images having different phases within the repetition period TR, and therefore, it is necessary to perform another imaging in addition to the imaging performed in a common routine examination.

An object of the present invention is to provide a technique that utilizes a multi-slice image widely used in routine examination to easily highlight the tissue such as the microbleeds (a designated region) which is hardly identified on 2D images.

Solution to Problem

In order to achieve the object above, the present invention utilizes a geometric feature of the designated region and a spatial feature in which the designated region is present, thereby highlighting the designated region. The spatial feature includes at least one of the followings; a distribution of surrounding tissues including the designated region (presence probability with respect to each tissue), and a spatial brightness distribution of pixel values of the designated region. The designated region includes a tissue such as a blood vessel and a lesion such as the microbleeds, and represents a portion that is specified as one region, according to characteristics of the tissue and the lesion.

That is, the MRI apparatus of the present invention comprises a reconstruction unit configured to collect magnetic resonance signals of an examination target and to reconstruct an image, and an image processing unit configured to process the image reconstructed by the reconstruction unit, to specify a region having a certain contrast (hereinafter, referred to as the designated region) included in the image. The image processing unit comprises a highlighting unit configured to highlight the designated region, based on shape information of the designated region and spatial information of the designated region. For example, the image processing unit includes a shape filtering unit and a spatial information analyzer, and the shape filtering unit acquires as the shape information, an image of a predetermined shape based on a geometric feature of the designated region. The spatial information analyzer utilizes an image of the predetermined shape to analyze the probability that the designated region exists in each tissue of the examination target, and brightness information of the predetermined shape.

The present invention also embraces an image processor having some or all the functions of the image processing unit in the above-described MRI apparatus.

Further, the image processing method of the present invention processes an image acquired by MRI and highlights the designated region included in the image, comprising a step of acquiring a candidate image of only a predetermined shape included in the image, and a step of acquiring spatial information of the predetermined shape, wherein the step of acquiring the spatial information includes at least one of a step of calculating a tissue distribution of the predetermined shape in the image, and a step of calculating a brightness distribution of the image of the predetermined shape.

The tissue distribution is information indicating how the surrounding tissues of the designated region are distributed, and the brightness distribution is information indicating a change in the brightness value of the designated region mainly due to the blooming effect.

According to the present invention, with respect to the designated region to be highlighted, the shape information obtained from the geometric features of the designated region is used, and further the spatial information such as the spatial distribution of the designated region is used. Accordingly, this allows the designated region to be automatically highlighted and presented even in 2D images.

DETAILED DESCRIPTION OF THE PREFERRED EMBODIMENTS

There will now be described embodiments of an MRI apparatus and an image processing method according to the present invention.

Figure 1:
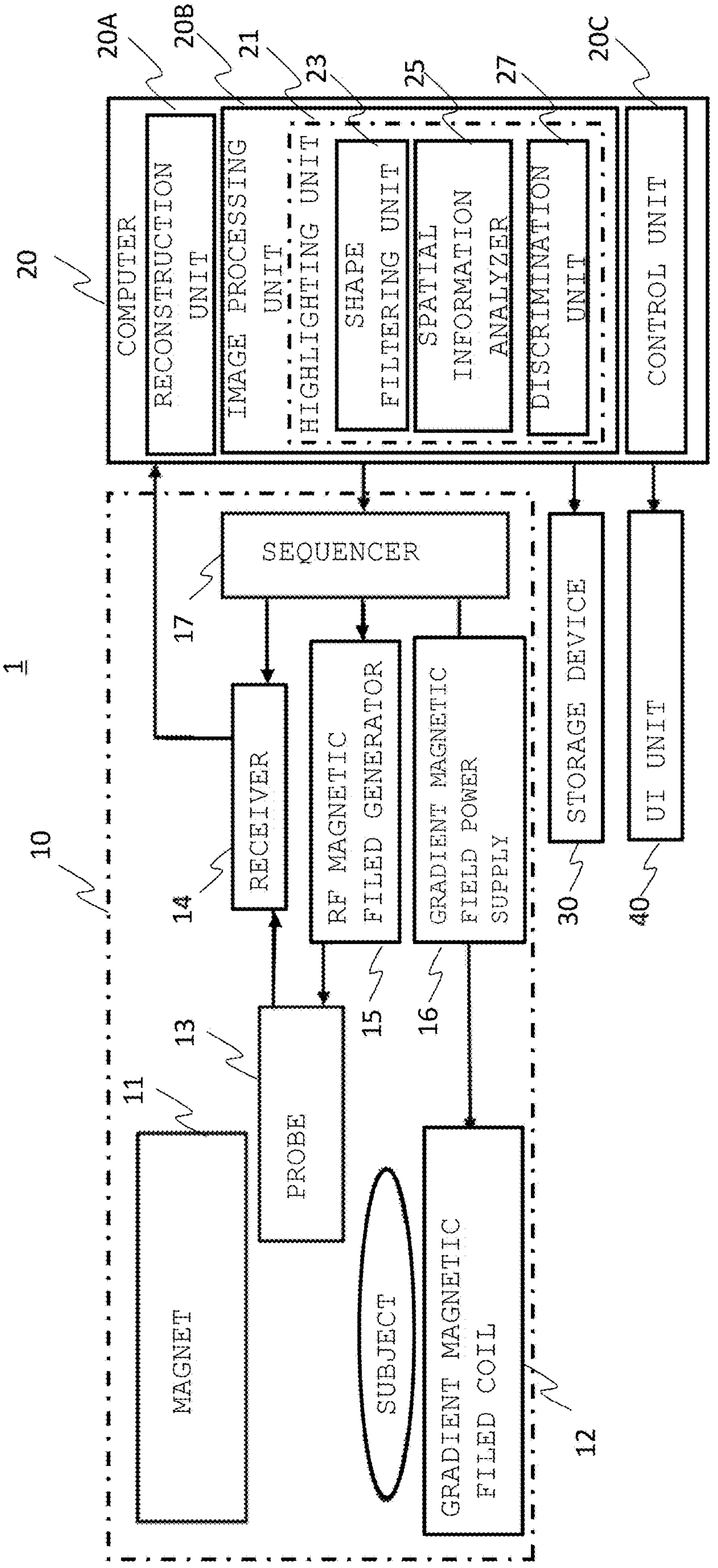
FIG. 1 is an overall configuration diagram showing an embodiment of an MRI apparatus of the present invention.

First, with reference to FIG. 1, a general outline of the MRI apparatus will be described. As shown in FIG. 1, the MRI apparatus 1 comprises a magnet 11 configured to generate a homogeneous static magnetic field in the examination space where a subject is placed, a gradient magnetic field coil 12 configured to provide a magnetic gradient with respect to the static magnetic field generated by the magnet 11, a probe 13 provided with a transmitting coil configured to apply a pulsed RF magnetic field to the subject and to cause nuclear magnetic resonance in nuclei of atoms constituting the tissue of the subject, and a receiving coil configured to receive a nuclear magnetic resonance signal generated from the subject, a receiver 14 connected to the receiving coil, an RF magnetic field generator 15 to which the transmitting coil is connected, a gradient magnetic field power supply 16 to which the gradient magnetic field coil 12 is connected, a sequencer 17 configured to control the receiver 14, the RF magnetic field generator 15, and the gradient magnetic field power supply 16 according to a predetermined pulse sequence, and a computer 20. Among the above-described elements, elements other than the computer 20 are collectively referred to as an imaging unit 10.

The nuclear magnetic resonance signals received by the receiver 14 of the imaging unit 10 are digitized and passed to the computer 20 as measurement data.

A structure, functions, and others of each unit constituting the imaging unit 10 are the same as those of publicly known MRI apparatuses, and the present invention can be applied to various known types of MRI apparatuses and elements. Thus, in here, the imaging unit 10 will not be described in detail.

The computer 20 is a machine or a workstation provided with a CPU, a GPU, and a memory, and has a control function (a control unit 20C) for controlling the operation of the imaging unit 10, and image processing functions (a reconstruction unit 20A and an image processing unit 20B) for performing various calculations on the measurement data acquired by the imaging unit 10 and on the image reconstructed from the measurement data. Each function of the computer 20 can be implemented, for example, when a CPU or a similar element uploads and executes programs of each function. Some of the functions of the computer 20, however, may be implemented by hardware such as a programmable IC (e.g., ASIC, FPGA). In addition, the functions of the image processing unit 20B may be implemented, in a remote computer connected to the MRI apparatus 1 by wired or wireless connection, or in a computer constructed on a cloud, and this type of computer (an image processor) is also embraced in the present invention.

The computer 20 includes a storage device 30 that stores data and results (including intermediate results) required for control and computation, and a UI (user interface) unit 40 that displays GUI and computation results to the user and accepts designations from the user. The UI unit 40 includes a display device and an input device (not shown).

The MRI apparatus of the present embodiment comprises a function (highlighting unit 21) in which the image processing unit 20B of the computer 20 highlights a particular tissue or region (hereinafter, referred to as a designated region) included in an image, using the image reconstructed by the reconstruction unit 20A. This function utilizes a geometric feature and spatial information of the designated region. For that purpose, the highlighting unit 21 comprises, for example, a shape filtering unit 23 that acquires an image of only a shape of the designated region, and a discrimination unit 27 that discriminates a specific tissue, using the image of only the shape acquired by the shape filtering unit.

The discrimination unit 27 uses one or more methods to make the discrimination. In one discrimination method, the discrimination unit 27 utilizes, as the spatial information, a result of analyzing a distribution (tissue distribution) of the designated region in the entire imaged tissue. In another method, the discrimination unit 27 utilizes, as the spatial information, a result of analyzing the brightness distribution of pixel values of the image having only the shape. In yet another method, the discrimination unit 27 makes the discrimination utilizing a CNN (Convolutional Neural Network) trained in advance using images including the designated region and the surrounding region (including the shape information and the spatial information of the designated region). The spatial information analyzer 25 as shown in FIG. 1 is a functional unit including algorithms or CNNs, for executing any one or more of several methods described above.

Figure 2:
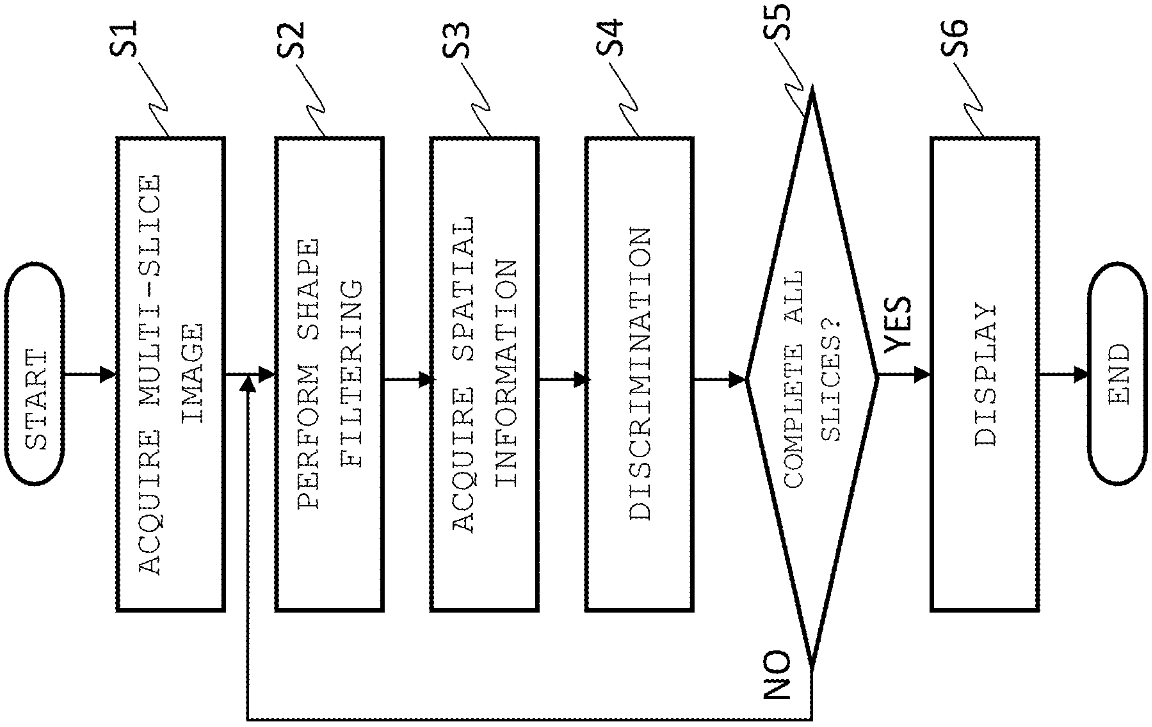
FIG. 2 illustrates an outline of the operation of the MRI apparatus shown in FIG. 1.

The processing of the image processing unit 20B will be described later. With reference to FIG. 2, there will be described an outline of the processing of the MRI apparatus including the image processing.

First, under the control of the control unit 20C, the imaging unit 10 performs imaging according to imaging conditions set in an examination protocol, or according to imaging conditions set by a user, and collects nuclear magnetic resonance signals for obtaining an image of the subject. The pulse sequence used for the imaging is not particularly limited, but here, multi-slice 2D imaging is performed in which an area having a predetermined thickness is divided into a plurality of sections (slices) and imaging is performed for each slice. In the multi-slice 2D imaging, the pulse sequence is repeated with changing the slice position to be selected, and a 2D image with multiple slices is acquired.

The reconstruction unit 20A performs an operation such as the fast Fourier transform using the image data of the respective slices to obtain an image for each slice (S1). Basically, the multiple cross sections are in parallel, but in addition, an image of a cross section orthogonal thereto may also be acquired.

The image processing unit 20B (the highlighting unit 21) performs a process to highlight the designated region included in the image with respect to each image of the multiple cross sections. For this reason, first, a shape filter is applied based on a geometric feature of the designated region, and an image of only the predetermined shape is created (S2). For example, when the designated region corresponds to microbleeds, the shape filtering unit 23 applies the shape filter for extracting a small circular shape (granular shape) to create an image of only the granular shape. In this case, it is also possible to use a combination of a plurality of shape filters in order to remove other shapes that may be mixed due to the use of only one shape filter.

Then, the spatial information analyzer 25 analyzes the image obtained as a result of the filtering, and acquires spatial information such as tissue distribution features of individual granular shapes (S3). The spatial information includes information (tissue distribution) of the surrounding tissue in which the granular shapes in the target portion are distributed, a distribution (brightness distribution) of the pixel values in the individual granular shapes, or a combination thereof.

The discrimination unit 27 uses the analysis result of the spatial information analyzer 25 to discriminate between the designated region that is a target of the discrimination and the tissue that is similar in shape to the designated region but is different from the designated region, and extracts only the designated region (S4). When the discrimination unit 27 makes discrimination using a CNN that has learned images including both the shape and the spatial features of the designated region, the shape filtering unit 23 and the spatial information analyzer 25 may be omitted.

The processing above is performed on all the slices of the multi-slice image (S5), and the positions and sizes of the designated region can be finally specified in the entire region to be imaged. The information of the specified designated region is displayed, for example, being superimposed on the entire image (S6). The entire image may be a T2* weighted image used for specifying the designated region, or may be another image acquired in parallel (for example, a susceptibility-weighted image or a proton-density weighted image).

The user checks the position of the designated region displayed on the image, and if the designated region indicates microbleeds or calcification, the user can confirm the location of the microbleeds or the calcification occurrence.

According to the present embodiment, regarding a tissue or a lesion that has been difficult to be discriminated in conventional 2D images, such designated region can be discriminated and highlighted in the 2D image acquired by a normal MRI examination, by using the shape information and the spatial information of the designated region.

Next, an embodiment of the process performed by the image processing unit will be described, taking as an example, the case where the designated region corresponds to microbleeds.

First Embodiment

In the first embodiment, the shape filtering unit 23 comprises a filter A for extracting a granular shape and a filter B for extracting a linear shape, and removes the shape extracted by the filter B from the shape extracted by the filter A to obtain an output of the shape filtering unit 23. Further, the spatial information analyzer 25 uses, as the spatial information of the designated region, information indicating in which portion the designated regions are distributed, in a plurality of organs or regions, and information obtained by analyzing the blooming effect (blurring or enlargement of a lesion outline due to a magnetic susceptibility effect of bleeding) of the granular shape extracted as the shape of the designated region. The discrimination unit 27 identifies the designated region based on the analysis result of the spatial information analyzer 25.

Figure 3:
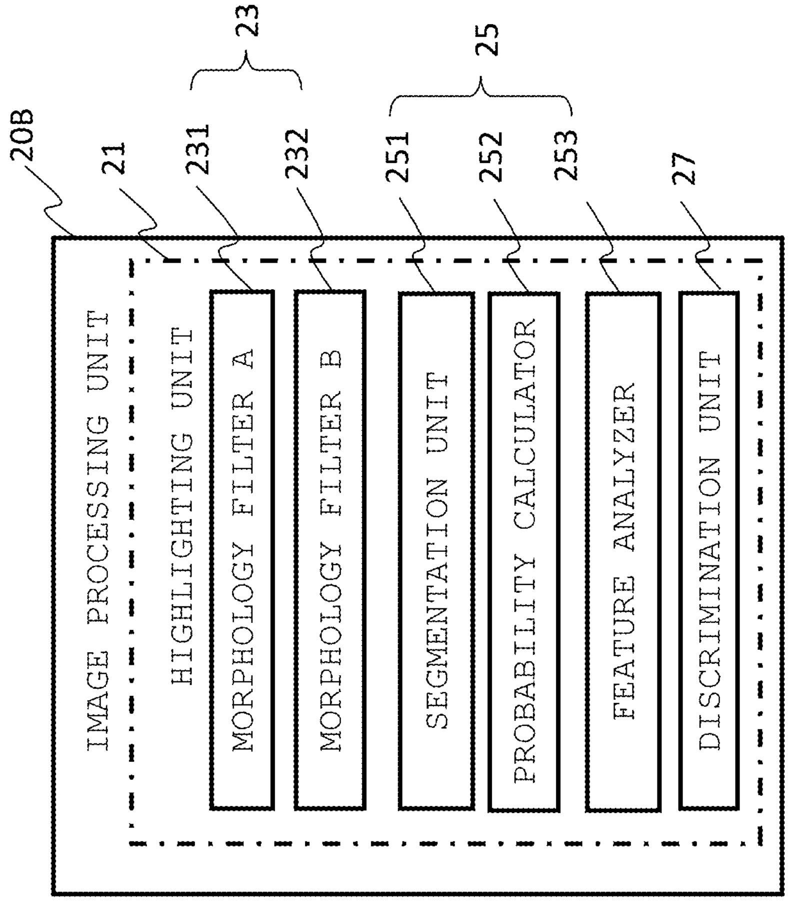
FIG. 3 is a block diagram of an image processing unit according to the first embodiment.
Figure 4:
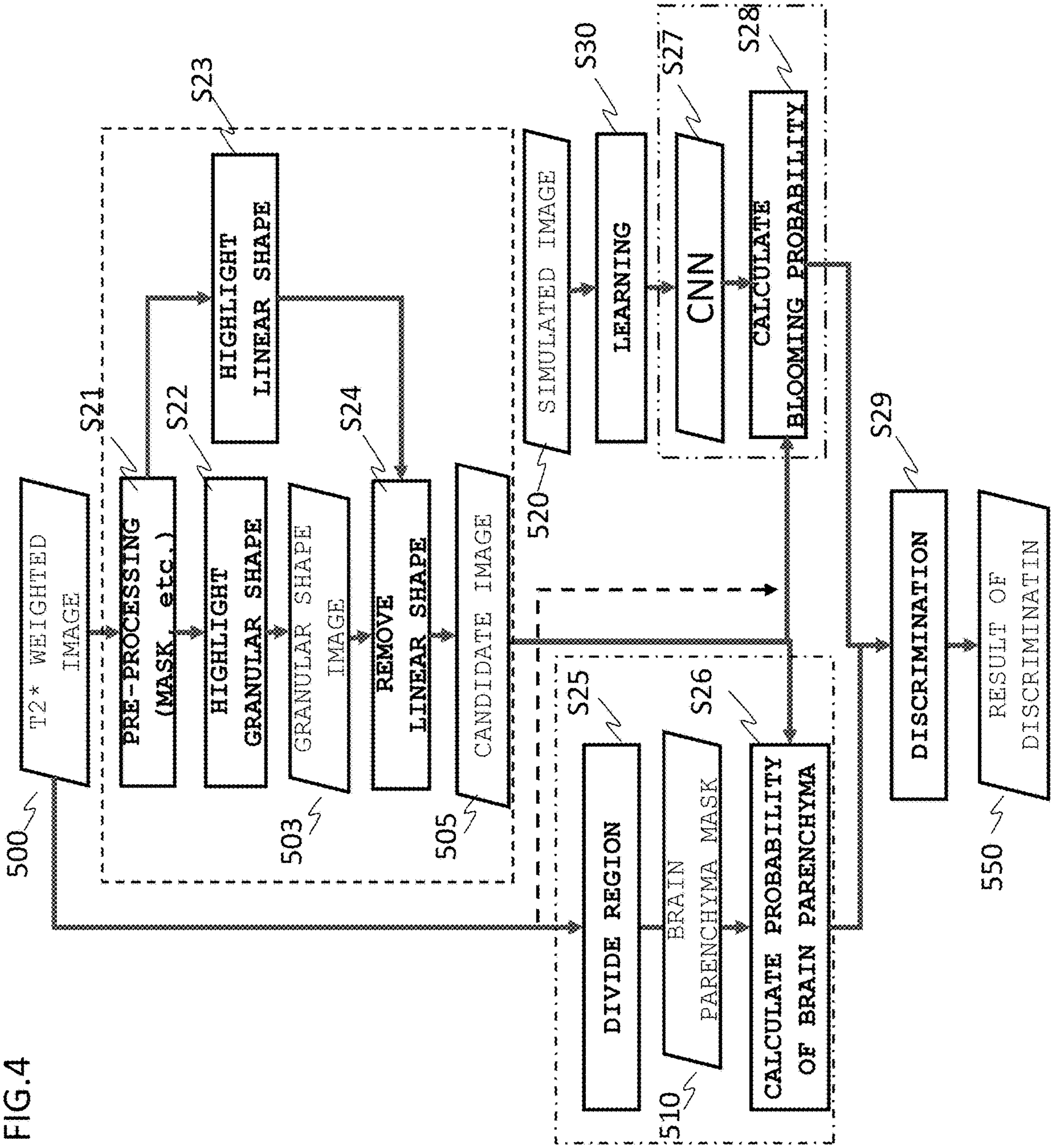
FIG. 4 illustrates an image processing flow according to the first embodiment.

With reference to FIGS. 3 and 4, there will be described detailed processing of the image processing unit 20B according to the present embodiment. FIG. 3 is a functional block diagram of the image processing unit 20B according to the present embodiment. In FIG. 3, the same components as those shown in FIG. 1 are denoted by the same reference numerals, and the description thereof will not be provided redundantly.

As shown in FIG. 3, the shape filtering unit 23 includes two types of morphology filters 231 and 232. One is a morphological filter A for extracting the granular shape, and the other is a morphological filter B for extracting the linear shape. The morphology filter is a technique for extracting a desired shape by a morphology operation combining expansion and contraction, and a publicly known algorithm can be used. For example, as an example of the morphological filter, a morphological filter bank may be used. The morphology filter bank is a processing that is based on the morphological operation for extracting features from a given image using the opening process or the top-hat transform (see IEICE Technical Report MI2010-101 (2011 January) for details). By repeating the process with changing the size of structural elements used for the morphological operation, granular (circular) components and linear components, each having a particular size and thickness, can be highlighted.

However, as long as the filter is capable of extracting a predetermined form, the Hough Transform, for example, may also be used without limited to the morphological filter. In addition to the two types of the filters, a filter for extracting features other than the shape may also be provided.

In order to acquire information indicating where the designated regions are distributed in the plurality of organs or regions, the spatial information analyzer 25 comprises a segmentation unit 251 that divides the image into the multiple organs or regions to create segmentation images with respect to each of the organs or tissues, and a probability calculator 252 that calculates the probability of the tissue in each of the segmentation images. The spatial information analyzer 25 is further provided with a feature analyzer 253 that analyzes the features of the predetermined shape and of the tissue surrounding the predetermined shape in order to analyze the blooming effect.

With reference to FIGS. 4 to 7, the processing of the image processing unit 20B having the above-described configuration will be described. Here, there will be described the case where the 2D image to be processed is a T2* weighted brain image. In FIG. 4, the processing surrounded by the dotted line indicates the processing of the shape filtering unit 23, the processing surrounded by the dashed-dotted line indicates the processing of the segmentation unit 251 and the probability calculator 252, and the processing surrounded by the dashed-two-dot line indicates the processing of the feature analyzer 253.

First, the shape filtering unit 23 receives a T2* weighted image (brain image) created by the reconstruction unit 20A, and performs pre-processing where regions (backgrounds) other than the brain are removed using a mask (the mask that makes the brain region 0 and the rest 1) and also noise reduction is performed (S21). As the noise reduction, a publicly known average filter can be used, for example. Although the pre-processing S21 is not essential, the accuracy of subsequent processing (filtering, and so on) can be improved by performing such pre-processing. There are various known methods (e.g., A hybrid approach to the skull stripping problem in MRI: Neuroimage, 2004 July; 22 (3): 1060-75) for extracting the mask of brain region, and any of these methods may be used.

Then, the shape filtering unit 23 applies each of the morphological filters A231 and B232 to the image of the brain region (S22 and S23), to obtain an image (granular image) 503 in which a granular shape (circular or elliptical) is extracted and an image in which a linear shape is extracted. The granular image 503 and the linear image (not shown) resulting from the process S23 are subtracted from each other, linear components are removed from the granular image 503 (S24), and an image having only the granular shape (grain-line difference image) is obtained as a candidate image 505. Alternatively, instead of the difference, the linear image is divided from the granular image for each pixel, and an image (grain-line division image) highlighting the granular component is obtained as the candidate image. Further alternatively, a threshold processing is performed on the grain-line difference image or the grain-line division image with an appropriate threshold value, whereby a binary image is calculated in which the circular region is 1 and otherwise 0, and the binary image may be used as the candidate image. By combining the two types of filters as described above, it is possible to prevent mixing of unnecessary shapes and to extract only the shape to be discriminated.

Figure 5:
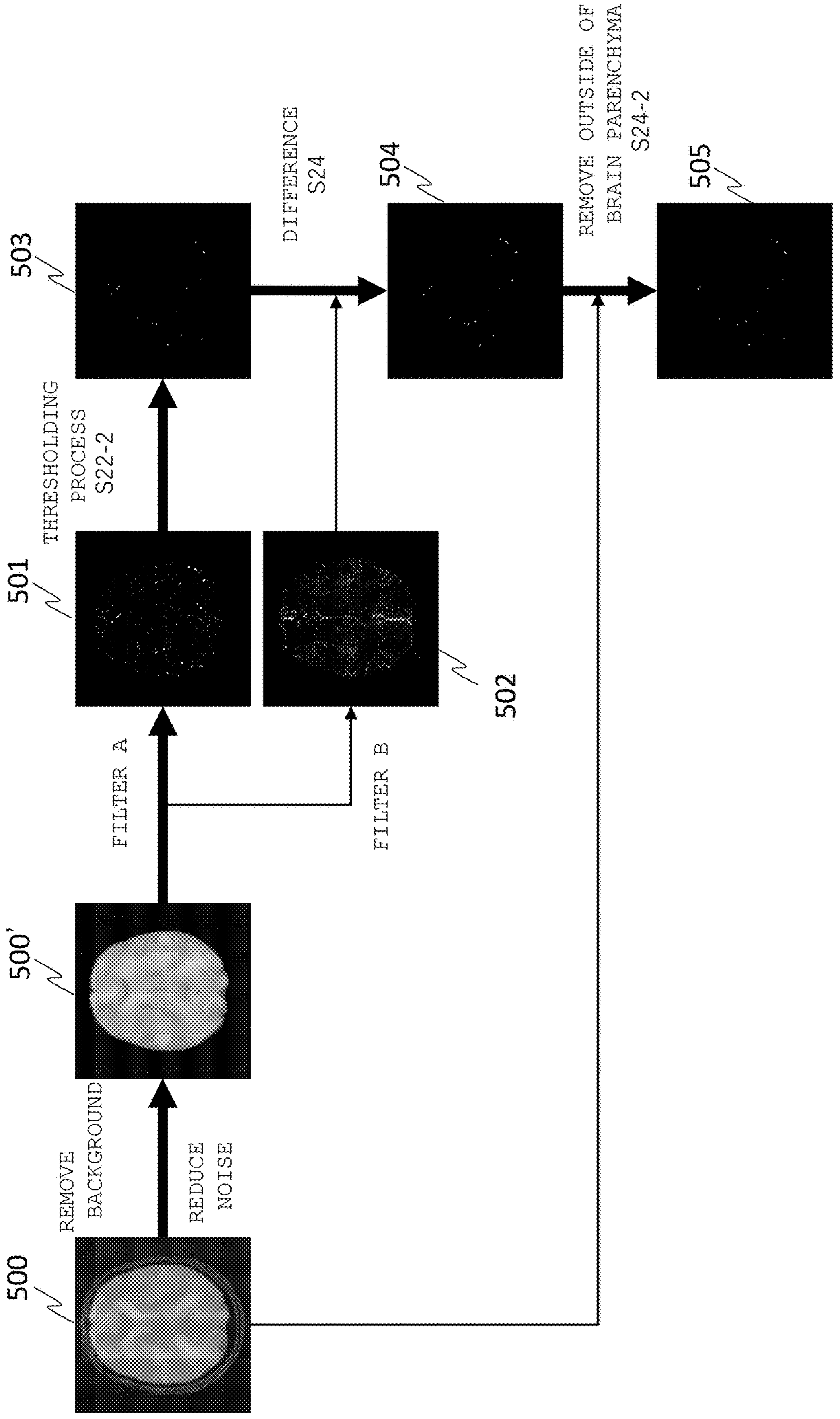
FIG. 5 illustrates the processing of a shape filtering unit.

Prior to obtaining this difference, as shown in FIG. 5, it is preferable to perform a thresholding process in which only an image having a predetermined pixel value or more is obtained from the filtered granular image 501, and to remove the tissue extracted as the granular shape having a pixel value smaller than the predetermined value, other than blood vessels and microbleeds (S22-2). The threshold processing may also be performed based on the size of the granular shape, together with the threshold processing of the pixel value or instead thereof. A targeted lesion of microbleeds is generally less than or equal to 10 mm in diameter, and thus circular or elliptical shapes exceeding the diameter 10 mm are excluded. Alternatively, the number of pixels in each cluster extracted by the threshold processing may be calculated, and the granular shape having not more than a predetermined number of pixels (for example, 10 pixels) may be removed.

It is further possible that the linear shape image 502 is subtracted from the granular image 503 after the thresholding processing, then the difference image 504 may be subjected to a process of removing the granular shape mixed from other than the brain parenchyma, using the pixel information of the original image 500 (S24-2). This processing divides the image 504 after the subtraction into small regions (small patches), determining whether a value obtained by multiplying an intermediate value of pixel values in each small patch by a predetermined coefficient, is smaller than an average value in the mask (e.g., the brain region) of the original image 500, and when the value is smaller, the patch (the granular shape included in the patch) is excluded. By adding this processing, it is possible to reliably exclude the granular shape in the region outside the brain. The coefficient multiplying the intermediate value is an adjustment coefficient for preventing excessive exclusion, and a value such as 0.8 is used, for example. Alternatively, a histogram within the small patch may be analyzed to exclude granular shapes that have characteristics different from normal vessels or microbleeds. For example, a value obtained by multiplying the minimum value of T2* weighted images in the small patch by a constant (for example, 0.8) (the minimum value in the patch) may be compared with the average value in the mask, and the granular shape having a larger minimum value in the patch (a granular shape with light contrast) may be excluded.

The processing in the shape filtering unit 23 has been described so far, and the image of only the granular shape existing in the brain is obtained as the candidate image 505 by the series of processing.

Next, the spatial information analyzer 25 analyzes the spatial feature of the granular shape of the candidate image 505. In the present embodiment, based on the findings that a half or more of the microbleeds are contained in the cerebral parenchyma, the region of the brain image is divided into the cerebral parenchyma and cerebrospinal fluid (CSF), and the probability maps are generated respectively as spatial information. For this purpose, the segmentation unit 251 first creates a segmentation image for each region from the brain image of the subject. As the image used for segmentation, FIG. 4 shows an example employing the T2* weighted image 500 that is used to create the candidate image, but the pre-processed image 500' may also be utilized. As long as the image is acquired for the same subject, and the white matter, gray matter, cerebrospinal fluid (CSF), and others are delineated with different contrasts, the brain image is not limited to the T2* weighted image, and for example, a T1 weighted image or a T2 weighted image may also be usable.

Figure 6:
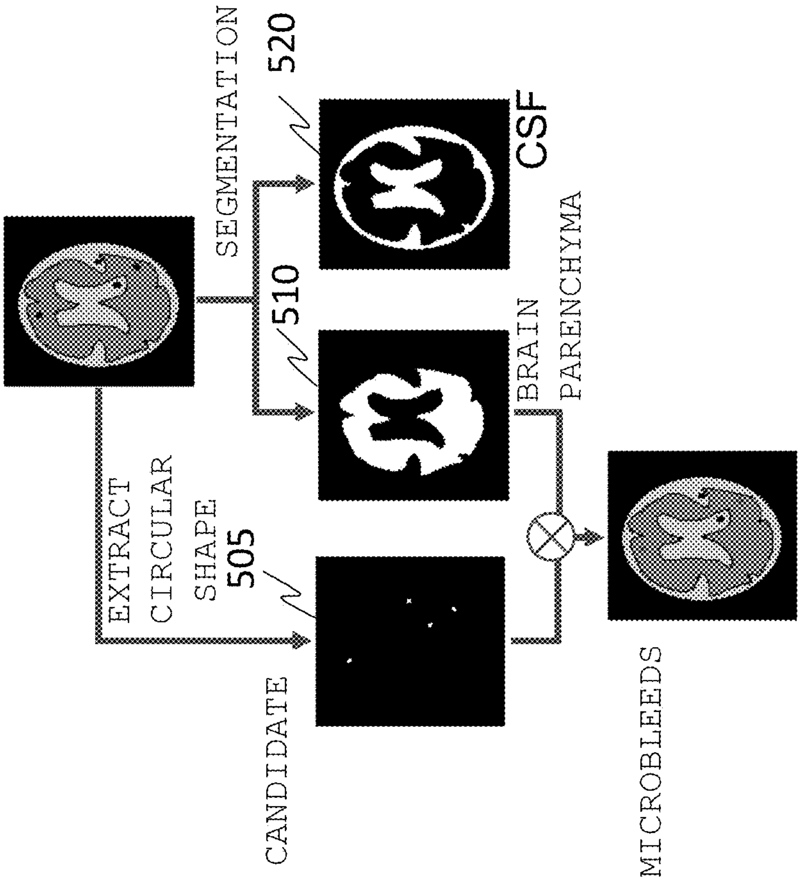
FIG. 6 illustrates the processing of a spatial information analyzer.

The segmentation is a technique for generating images (segmentation images) divided for respective tissues, based on the features of each tissue appearing in the image, and there are known various algorithms such as the k-means method, the region growing method, and the nearest neighbor algorithm, and also methods that employ CNNs, and any of them may be adopted. In the present embodiment targeting the brain image, as shown in FIG. 6, the segmentation unit 251 creates the brain parenchyma image 510 and the CSF image 520, by segmenting the brain image.

Next, the probability calculator 252 calculates the probability that the granular shape of the candidate image is included in the cerebral parenchyma, and the probability that the granular shape of the candidate image is included in the CSF (S26). Specifically, as shown in FIG. 6, the candidate image 505 is mixed with the brain parenchyma image (brain parenchyma probability map) 510 to calculate the probability that the granular shape exists in the brain parenchyma. Similarly, the candidate image 505 is mixed with the CSF image (CSF probability map) 520 to calculate the probability that the granular shape exists in the CSF.

The segmentation followed by calculating the probability is performed in this way, and it is possible to accurately discriminate the spatial information of the microbleeds that are unevenly distributed in certain portions.

On the other hand, when the candidate image 505 is inputted, the feature analyzer 253 analyzes the features of the microbleeds with respect to the individual granular shapes. Several methods of the analysis may be adopted, and in the example as shown in FIG. 4, the CNN is used (S27). For example, the CNN has learned using as training data, a large number of combinations (simulation images 530) of images of microbleeds and images of blood vessels created by simulation, to calculate the probabilities of blooming (blurring or enlargement of the lesion outline due to the magnetic susceptibility of bleeding) in response to an input data (image). In creating the images by simulation, for example, a simple circular image may be used as the simulated image of the blood vessel, and then a Gaussian filter is applied to the circular image, thereby obtaining another circular image with a smoothed outline as the simulated image of microbleeds. Alternatively, with a spherical model assuming a constant magnetic susceptibility value, a local magnetic field variation is calculated so as to create the simulated image of microbleeds. It is to be noted that the images used for the CNN learning are not limited to the simulated images, but actually captured images may also be used. The CNN learning may be performed in the image processing unit 20B, or may be performed in a processor other than the image processing unit 20B.

The feature analyzer 253 applies the CNN to the candidate image 505, and calculates the probabilities of blooming for the individual granular shapes. In the above description, the CNN is applied to the candidate image 505, but a small region corresponding to each of the granular shapes in the candidate image 505 may be cut out from the original image (T2* weighted image) 500, and the CNN may be applied to the image patch (FIG. 4: dotted arrow). As described above, the candidate image 505 is an image obtained by extracting only the granular shapes by filtering (the granular shape images). Since the original image 500 is, however, left with the outline information as it is, the blooming probability may be calculated more accurately depending on the CNN learning data type.

In addition to calculating the probability of blooming, the feature analyzer 253 may calculate statistic values such as a diameter and a volume of the discriminated granular shape. As for the diameter, for example, the lengths of lines crossing the granular shape in two or more directions are measured, and the length of the longest line is defined as the diameter. As for the volume, if the granular shape identified as the microbleeds remains in only one slice, it may be approximately calculated from the diameter and the slice thickness, by approximating the microbleeds to a sphere or a cylinder. If the granular shape identified as the microbleeds is placed at substantially the same position of multiple slices, the volume may be approximately calculated from the diameter of the granular shape obtained for each slice and the thickness of the cross section covered by the multiple slices.

The discrimination unit 27 integrates the result calculated by the probability calculator 252 and the result calculated by the feature analyzer 253 as described above, and determines whether the granular shape of the candidate image (or the image patch obtained by cutting out the region corresponding to the granular shape from the original image) is microbleeds or a normal blood vessel. For example, the probability of existing in brain parenchyma calculated by the probability calculator 252 is subjected to threshold processing to discriminate between the two types. For example, if the probability is 50% or more, it is discriminated as the microbleeds, and if the probability is less than 50%, it is considered as the normal blood vessel. Similarly, if the blooming probability calculated by the feature analyzer 253 is equal to or larger than a predetermined threshold value, it is determined as the microbleeds. The discrimination unit 27 integrates both results. The integration method may be, for example, taking AND of both results (the result of the probability calculator 252 and the result of the feature analyzer 253), and only those determined to be microbleeds in both may be discriminated as the microbleeds. Alternatively, taking OR of the two results, those determined to be microbleeds in either one may be included as microbleeds. Alternatively, the probabilities of both types may be multiplied.

Finally, thus obtained discrimination result 550, i.e., the information of the microbleeds (information such as the number, the positions, the sizes of the microbleeds) is presented to the user. As the presentation method, various methods can be adopted, such as showing portions of the microbleeds with a different contrast or color, superimposed on the original T2* weighted image, and displaying the information such as the number and sizes of the microbleeds together with the image. Examples of such methods are shown in FIGS. 7 and 8.

Figure 7B:
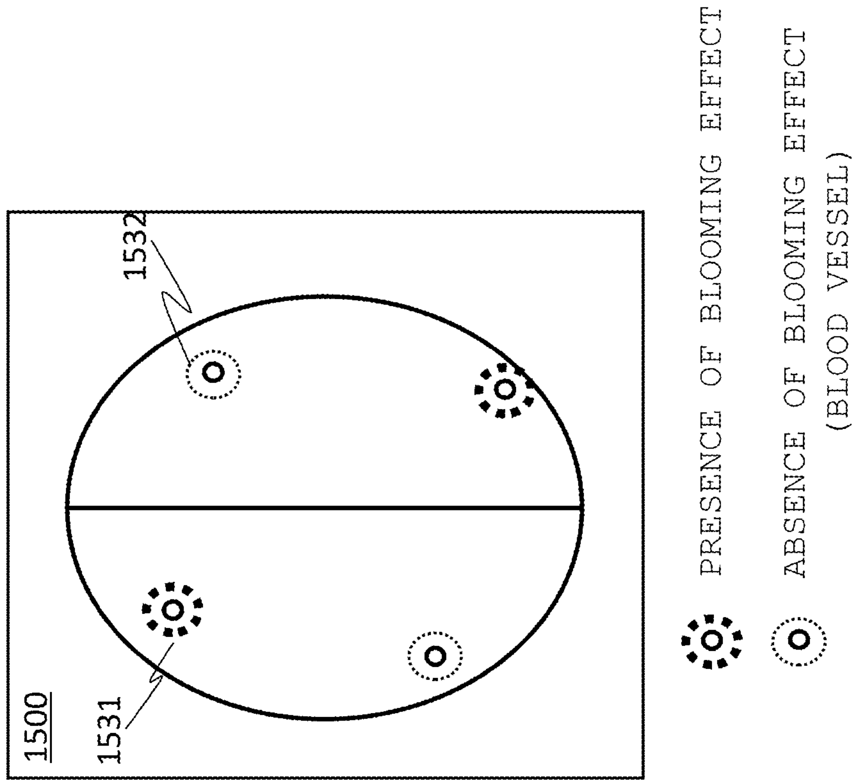
FIGS. 7A and 7B illustrate an example of a discrimination result according to the first embodiment.
Figure 7A:
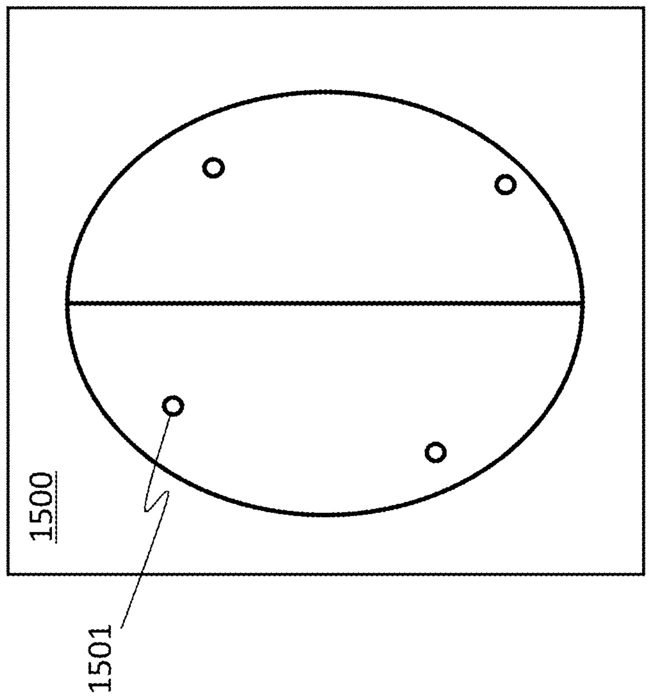

FIG. 7A is an example in which the results obtained by filtering in the original image 1500 (the granular shapes 1501 discriminated as the microbleeds and the granular shapes discriminated as the normal blood vessels) are displayed by different colors, for example, and FIG. 7B is an example in which marks 1531, 1532, and so on, for distinguishing between the microbleeds and the normal blood vessels are further attached and displayed. When the feature analyzer 253 calculates statistic values such as the diameters and the volume of the granular shapes, the statistic values may be reflected in the sizes of the marks 1531 and 1532.

Figure 8A:
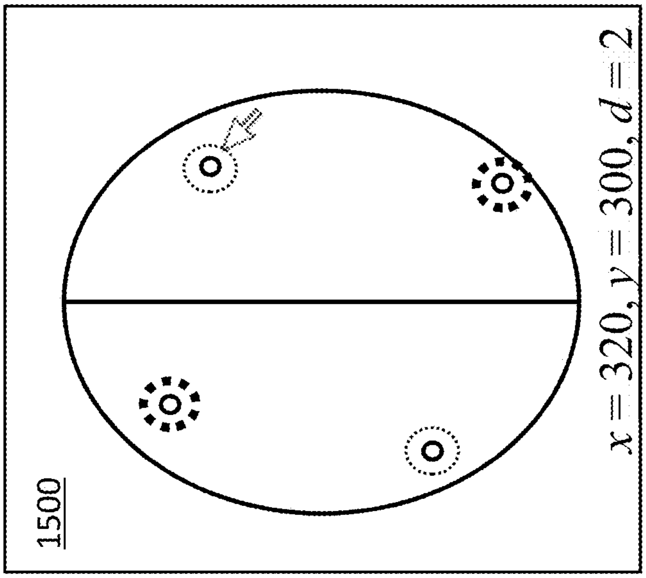
FIGS. 8A and 8B illustrate another example of the discrimination result according to the first embodiment.
Figure 8B:
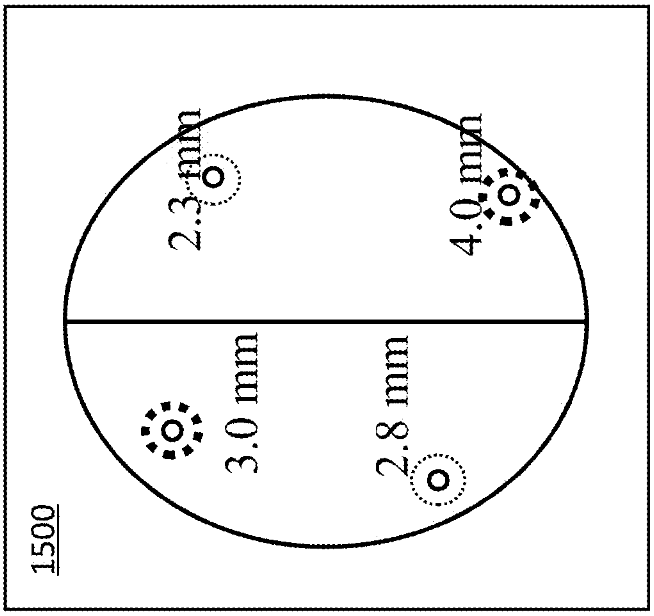

FIGS. 8A and 8B show further examples of displaying the statistic values such as the diameters and the volume of the granular shapes. FIG. 8A shows an example where the statistic values of the point indicated by the cursor is displayed at a position not overlapping the image (in a lower part in this case), and FIG. 8B shows an example that directly displays the statistic values respectively at the positions of the granular shapes after discriminated. By displaying the statistic values together in this way, it is possible to grasp not only the positions of the microbleeds but also the sizes thereof, also confirming whether or not the discrimination result is appropriate.

As described so far, the image processing unit 20B of the present embodiment targets the 2D-T2* weighted image, where the shape filtering unit 23 uses the filter A for filtering the granular shape and the filter B for filtering the linear shape to create the image of only the granular shape as the candidate image. The spatial information analyzer uses the segmentation images created from the image of the same subject to calculate the tissue distribution (the cerebral parenchyma probability and the CSF probability) of the candidate image, and calculates the blooming probability of the respective granular shapes. The discrimination unit 27 uses the analysis result of the spatial information analyzer 25 to perform the threshold processing on the candidate image, and identifies the granular shape having a high likelihood of microbleeds.

As described above, in addition to the geometric features appearing in a 2D image, the spatial feature of the extracted shape is used for discriminating and highlighting the microbleeds having been difficult to be discriminated in the 2D image conventionally. Further, the discrimination is performed for each of the multi-slice images, thereby grasping three-dimensional features together.

Modification of First Embodiment

There will now be described a modification of the processing of the image processing unit 20B on the basis of the first embodiment. In the following modification, the same elements and processes as those in the first embodiment will not be described redundantly, and mainly different points will be described.

Modification of 2D Image

In the first embodiment, a T2* weighted image is used as the source image for creating the candidate image. On the other hand, quantitative susceptibility mapping (QSM) or a susceptibility weighted image (SWI) is known as an image that is excellent in visualizing blood, and these images can be used instead of the T2* weighted image. Imaging methods and calculation methods for acquiring the QSM and SWI are known in the art, and therefore will not be described. In the QSM, when a value of cerebral parenchyma is assumed as 0, calcified tissue becomes relatively a “negative” (diamagnetic) value, and the tissue of microbleeds becomes a “positive” (paramagnetic) value, so that not only discrimination of the microbleeds but also discrimination of calcified tissue is possible.

It is also possible to use the QSM image or the SWI supplementarily at the time of discrimination, for example, as an image at the time of generating segmentation images, rather than as the original image of the candidate image.

First Modification of Feature Analyzer

In the first embodiment, the trained CNN is used to determine the blooming effect. Instead, a gradient of brightness change, or a low-rank approximation may be used as a tool for analyzing the blooming effect.

Figure 9:
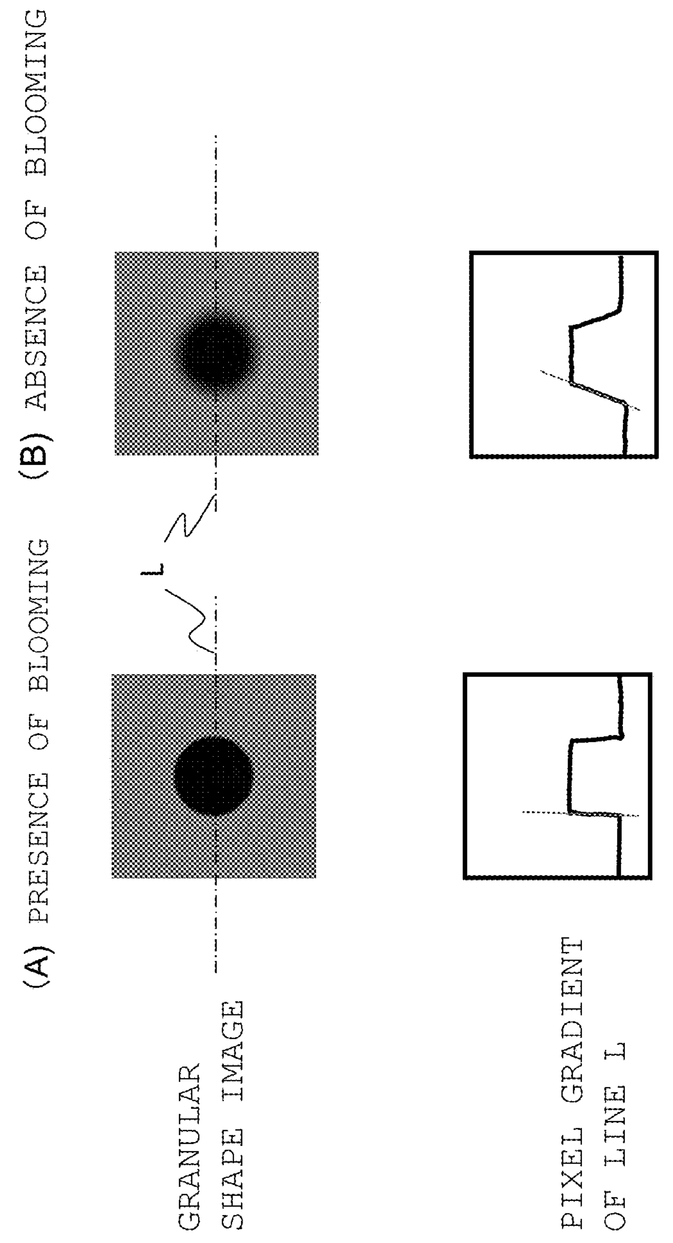
FIG. 9 illustrates a modification of the processing of a feature analyzer according to the first embodiment.

As for the gradient of the brightness change, as shown in FIG. 9, in the case of the blood vessel, internal signal values (pixel values) are clearly distinguished from the surrounding pixel values by the effect of the blood flow, and the edge of the outline is steep. On the other hand, in the case of the microbleeds, since the edge of the circular outline becomes blunt due to the susceptibility effect, causing a difference in gradient, and this is usable for the discrimination.

In this case, the feature analyzer 253 obtains the distribution (brightness distribution) of the pixel values of the line L passing through the center of the granular shape, and the gradients of the rising and the falling of the distribution are calculated from the distribution. In the case where the feature analyzer 253 calculates the diameter of the granular shape as a statistic value, the line as to which the diameter has been obtained among multiple lines, may be used as the line L passing through the center of the granular shape. The gradients obtained for respective granular shapes are subjected to the threshold processing, and the probability of the microbleeds is calculated and outputted from the feature analyzer 253.

Low-rank approximation is a technique to compress the dimension of data by singular value decomposition by limiting the number of singular values. An image (matrix) is expressed only by a fixed number of base images, whereby the dimension is reduced, and then it is possible to calculate the probabilities of two kinds of granular shapes (blood vessel or microbleeds, etc.) robustly against noise and error.

The discrimination using the blooming probability obtained by the methods of the aforementioned modification is the same as the first embodiment. These methods do not need the CNN learning, and thus the methods can be easily implemented in the image processing unit.

Second Modification of Feature Analyzer

The present modification features that there are prepared a plurality of tools for calculating the blooming probability in response to imaging conditions.

The size and shape of the blooming depicted in MR images may vary depending on the imaging conditions such as the static magnetic field strength, TE, and the direction of application of the static magnetic field (relative to the slicing direction). Therefore, there is a possibility that trained CNN and the feature analysis method assuming only one imaging condition cannot guarantee the certainty of the analysis result. In the present modification, multiple CNNs are prepared in response to a plurality of imaging conditions, and a CNN corresponding to the imaging conditions at the time of acquiring the target image is selected and used. In the case where the feature analyzer 253 uses the low-rank approximation, not the CNN, multiple base images are prepared, and the probability calculation using the low-rank approximation is performed with different base images depending on the imaging conditions.

The CNN or the base image may be selected by reading information of the imaging conditions associated with the image to be processed, and the image processing unit 20B may automatically determine the selection based on the information. Alternatively, options are presented to the user via the UI unit 40 so that the user can perform the selection.

Modification of Designated Region to be Applied

In the first embodiment, for the purpose of discriminating the microbleeds occurring in the brain parenchyma, the shape filtering unit 23 uses two types of filters; the filter for the granular shape and the filter for the linear shape. In order to discriminate a linear region such as the hemosiderin deposition in a brain surface, the shape filtering unit 23 uses the filter for the linear shape as the main filter. If necessary, as in the first embodiment, there may be used filters such as a filter for removing a mixed-in shape other than the linear shape and a filter for limiting the length of the linear region.

When the hemosiderin deposition in the brain surface is a target, the spatial information analyzer 25 calculates a pia mater probability map as the spatial information, from a pia mater segmentation image (an image of the region excluding brain parenchyma and CSF, or a border area between the brain parenchyma and the CSF). The presence or absence (probability) of the blooming effect is calculated as in the first embodiment. Then, the result of the pia mater probability and the result of the blooming probability are integrated to make the discrimination.

Second Embodiment

In the first embodiment, the spatial information analyzer 25 calculates the probability of the candidate image in each tissue and the blooming probability, and the discrimination unit 27 makes discrimination on the candidate image based on the result. The present embodiment features that the discrimination unit 27 uses a trained CNN by using learning data obtained by annotation for the designated region including spatial information.

Figure 10:
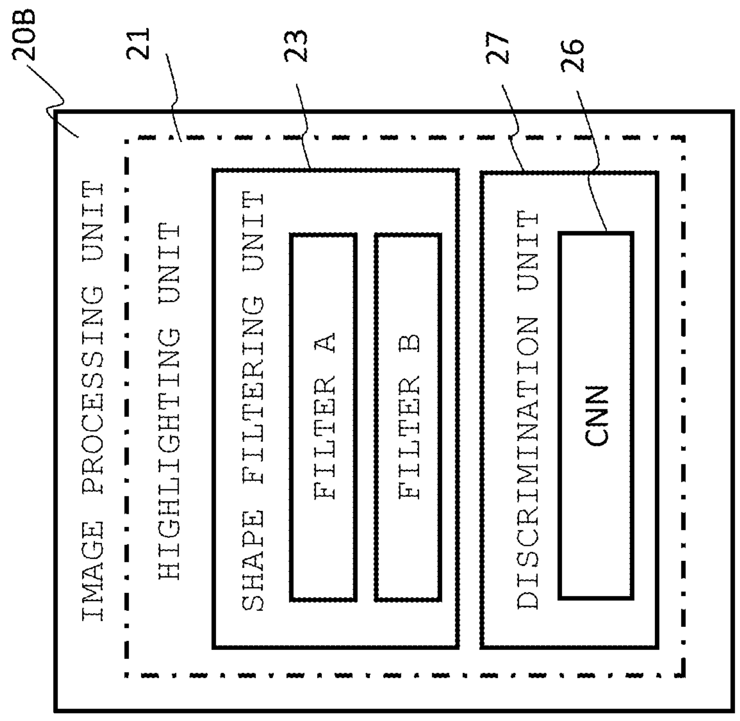
FIG. 10 is a block diagram showing the image processing unit according to a second embodiment.

Therefore, as shown in FIG. 10, the image processing unit 20B of the present embodiment is not provided with the spatial information analyzer 25 including the segmentation unit 251, the probability calculator 252, and the feature analyzer 253 as shown in FIG. 3. Instead, the trained CNN 26 functioning as the spatial information analyzer 25 is added. Other configurations are the same as those of the first embodiment.

A target of the annotation of the CNN 26 is a normal structure image, including a normal structure (here, a blood vessel) and its surrounding tissue. By using a large number of such patch images as learning data, it is possible to learn the normal structure images including information of the surrounding tissues. The CNN 26 is trained using this learning data to output the probability that the inputted image is the normal structure, or the probability that the inputted image is a non-normal structure (e.g., a lesion like microbleeds). Learning of the CNN 26 may be performed by the image processing unit 20B or by a computer other than the image processing unit 20B.

Figure 11:
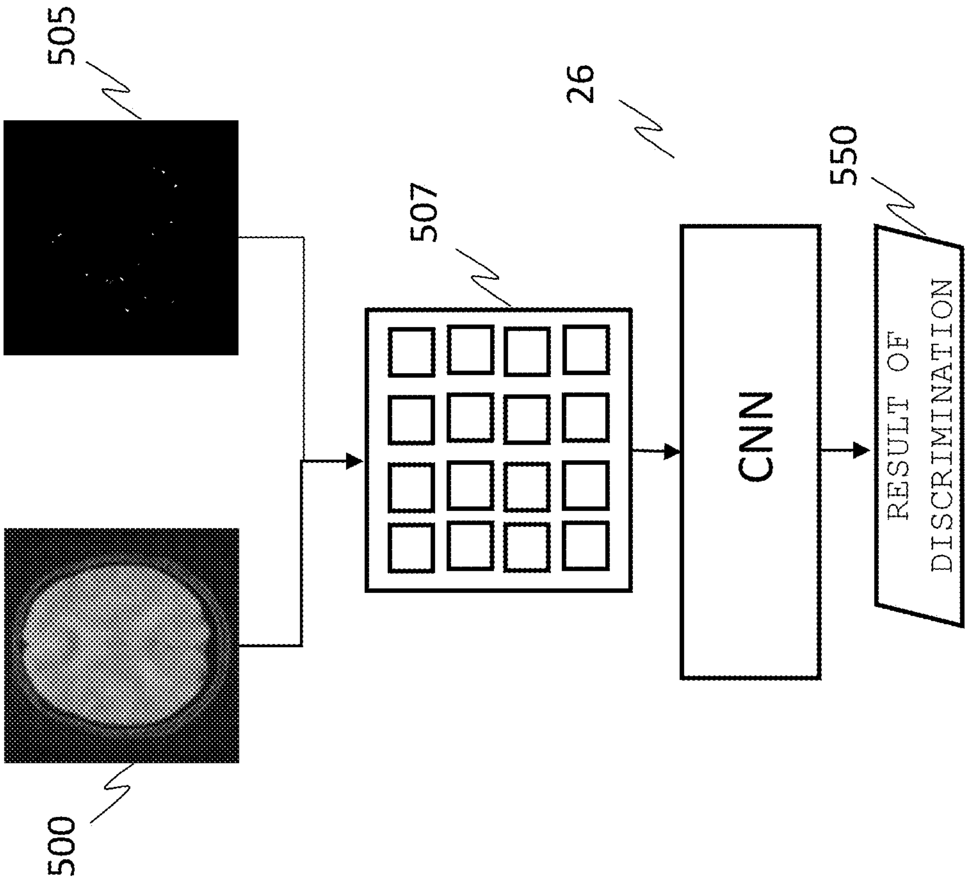
FIG. 11 illustrates the processing of the discrimination unit according to the second embodiment.

As shown in FIG. 11, the discrimination unit 27 inputs the original image 500 together with the candidate image 505 created by the shape filtering unit 23, and creates patch images 507 including granular shapes and its surrounding tissue, from the patch images of the candidate image 505 and the original image. The CNN 26 uses the patch images as inputs, and outputs the probability as being the normal structure or the probability as being the non-normal structure. Threshold processing is carried out based on these probabilities to make discrimination between the blood vessel and non-blood vessel, and the result is presented. A method of the presentation is the same as that of the first embodiment.

According to the present embodiment, the use of the trained CNN allows elimination of two processing lines of the spatial information analyzer 25; i.e., the tissue distribution (probability) calculation using the segmentation, and the blooming probability calculation. Thus, it is possible to simplify the processing of the discrimination unit 27.

Modification of Second Embodiment

In the second embodiment, the shape extraction and the discrimination are performed in two stages, and the candidate image created through filtering by the shape filtering unit 23 is subjected to the CNN processing. The CNN may also be used for the processing that includes the shape extraction.

In this case, the shape filtering unit 23 as shown in FIG. 10 is not provided, and the CNN 26 functions as both the shape filtering unit and the spatial information analyzer. The learning data of the CNN 26 may include, for example, patch images of “circular regions with blooming” and “circular regions in brain parenchyma”, and the CNN 26 is trained to output the probability that the input image corresponds to any of the patch image. In applying the CNN, after the original 2D image 500 is pre-processed, the patch images cut out from the pre-processed image 500' are inputted into the CNN 26, and the CNN 26 outputs the probabilities such as the probability that the “circular region with blooming” exists in the patch image, and the probability that the “circular region in cerebral parenchyma” exists in the patch image.

According to the present modification, it is possible to perform tasks for the CNN learning in another image processing unit in advance, and this facilitates the discrimination process by the image processing unit 20B.

Third Embodiment

The present embodiment features that there is added a means enabling a modification on the processing result of the image processing unit 20B, from a viewpoint of a user (such as a doctor and an examiner). Other configurations are the same as those of the first or the second embodiment, and redundant description will not be given. However, the drawings used in describing the first and the second embodiments will be referred to as necessary.

Figure 12:
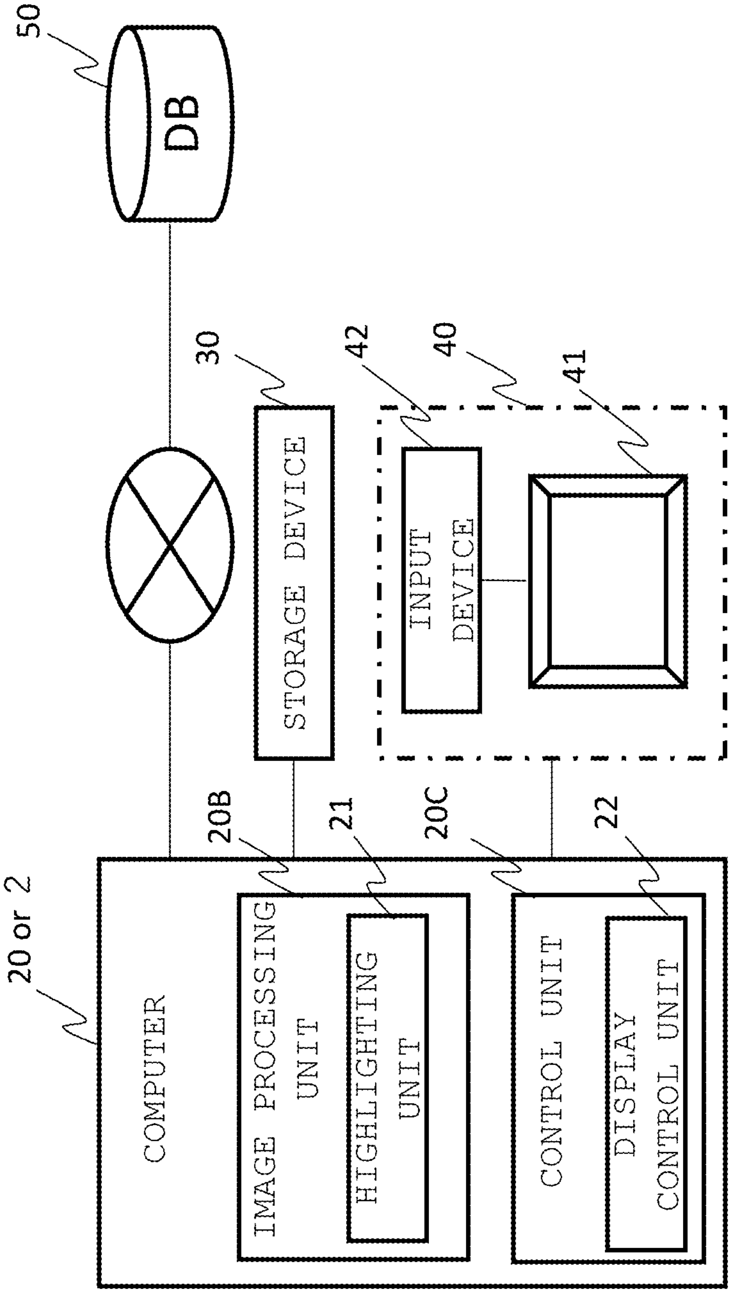
FIG. 12 illustrates the configuration of a third embodiment.

As illustrated in FIG. 12, the computer 20 of the MRI apparatus 1 or the independent image processor 2 is connected to the UI unit 40 including a storage device 30, an input device 42, and a display device 41, as in a typical computer. The display control unit 22 of the control unit 20C causes the display device 41 to display MR images created by the image processing unit 20B and the processing results of the highlighting unit 21, as shown in the display examples of FIGS. 7 and 8. The MR images and the processed images are stored in the storage device 30 as needed. They may also be transferred to an externally provided database such as Picture Archiving and Communication System (PACS) 50 via a communication means.

Figure 13:
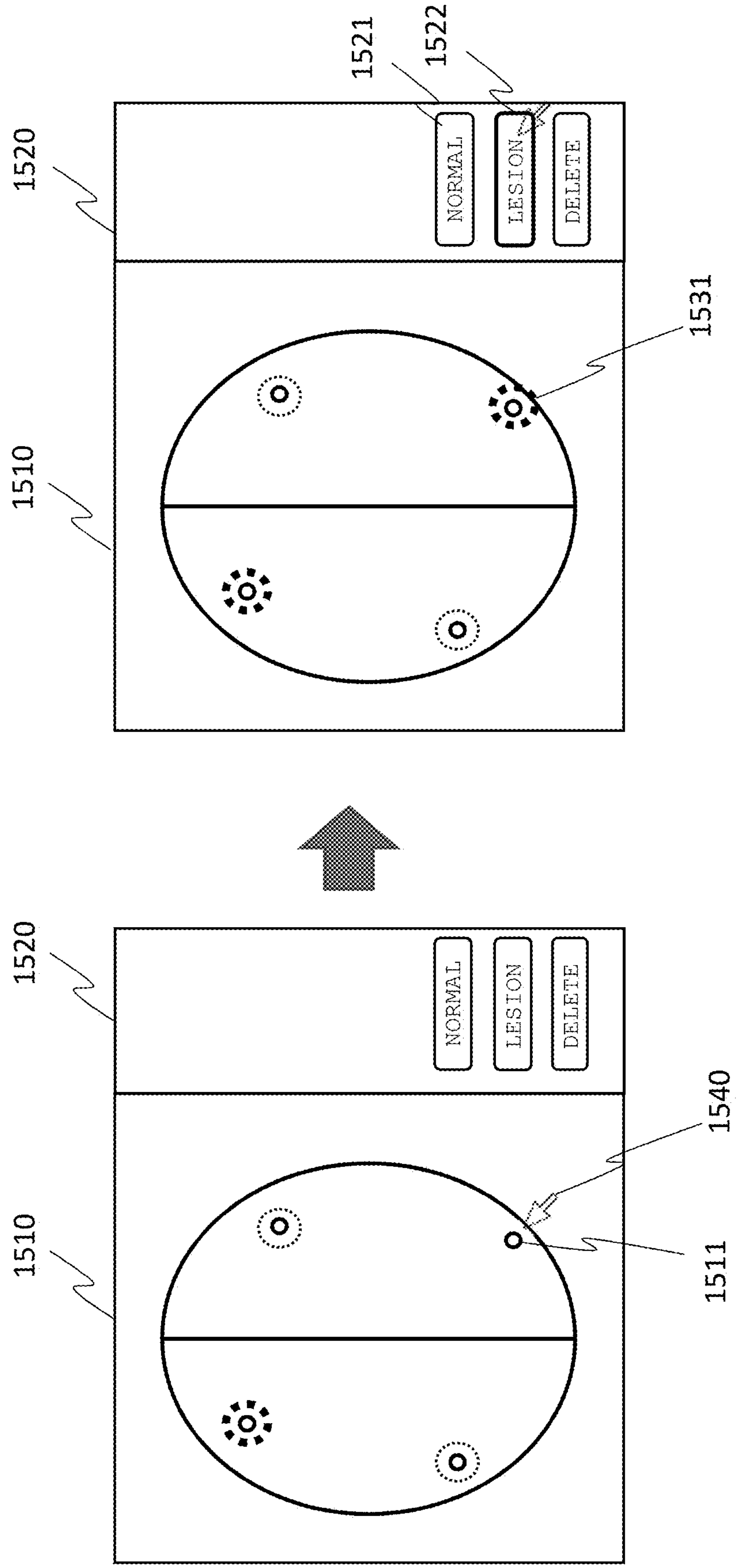
FIG. 13 illustrates a display example 1 of a display screen according to the third embodiment.

The display control unit 22 of the present embodiment provides a GUI for enabling the user to edit images displayed on the display device 41. For example, as shown in FIG. 13, the operating block (GUI) 1520 for “editing” is displayed together with the display block 1510 of the image showing the discrimination result. In the operating block, there are displayed, for example, the GUIs for accepting editing functions, such as a button “normal” for changing the discrimination result as a lesion to the discrimination result as a normal blood vessel, a button “lesion” for changing the discrimination result as a normal blood vessel to the discrimination result as a lesion, and a button “delete” for deleting the two types of discrimination results. Though not illustrated, a cursor for selecting a region and so on, and a button “select” for accepting the selection may be displayed (the selection may be confirmed through an input means such as a mouse). Further, those in the figure are shown by way of example, and other buttons such as a button for recalculating the statistic values and a button for updating a record or accepting the record may also be displayed. The image processing unit 20B receives the modification on the discrimination result through such operation of the GUI.

FIGS. 13 to 16 illustrate examples for modifying the discrimination result. In the example shown in FIG. 13, when a doctor or an examiner views the original T2* weighted image and decides that the granular shape 1511 corresponds to the microbleeds or blood vessel, though having not been determined as the microbleeds or blood vessel in the discrimination result, for example, the cursor 1540 is moved to the position of the granular shape 1511 to select the granular shape by the operation such as mouse-clicking, and then the "lesion" button 1522 is further operated. With this operation, the information is added to the discrimination result and reflected in the display. If the indication of the microbleeds is to be highlighted with a color different from other tissues, then the selected granular shape is additionally colored with this color and highlighted. If the indication of the microbleeds is to attach the mark 1531, the mark 1531 is attached to the selected granular shape. In the case of decision that the granular shape is a normal blood vessel, the same action is performed by using the "normal" button 1521 instead of the "lesion" button 1522, and the mark of the normal blood vessel is attached.

Figure 14:
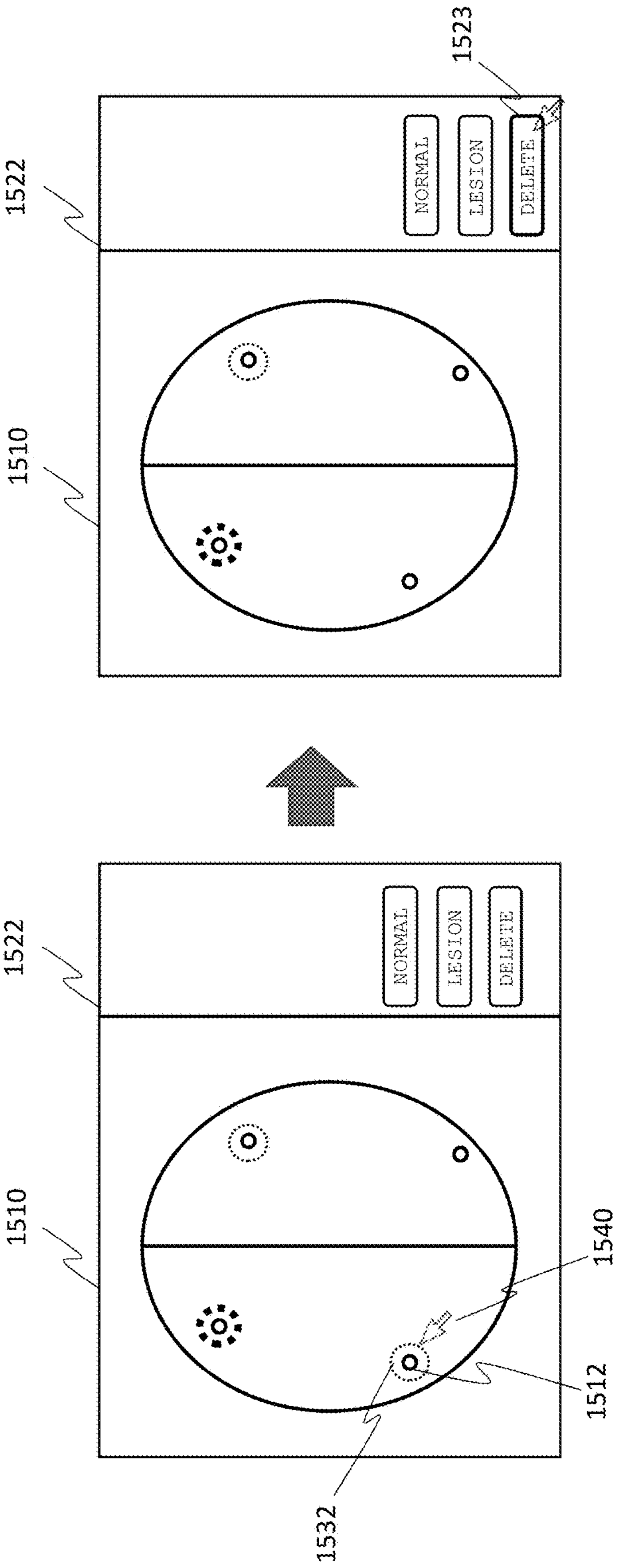
FIG. 14 illustrates a display example 2 of the display screen according to the third embodiment.

On the other hand, as shown in FIG. 14, when the user, such as the doctor and the examiner, decides that the region 1512 is not "microbleeds" nor "blood vessel", having been identified as the "microbleeds" or "blood vessel" in the discrimination result, the granular shape (region 1512) is selected as in the example of FIG. 13, and the "delete" button 1523 is operated. Then, the display control unit 22 deletes the color or the mark 1531 attached to the region 1512, and passes the information to the image processing unit 20B.

Figure 15:
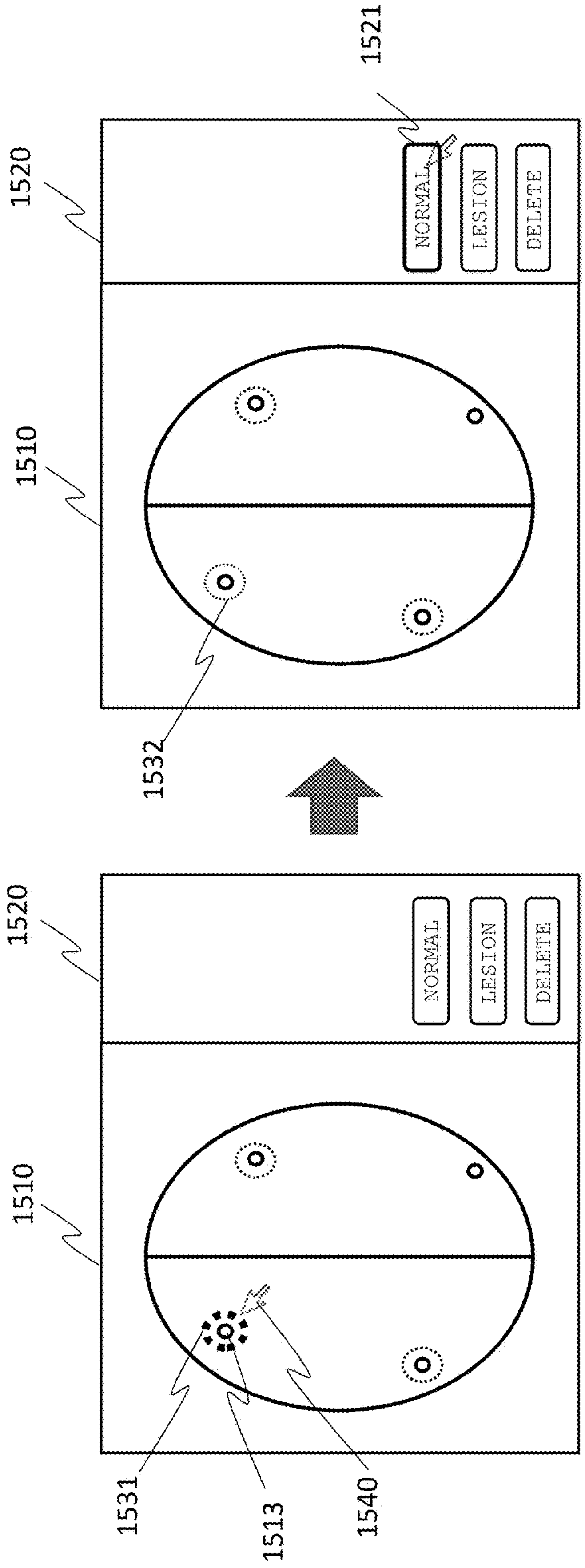
FIG. 15 illustrates a display example 3 of the display screen according to the third embodiment.

FIG. 15 is an example showing that the result of the discrimination unit 27, determined as the microbleeds, is changed to the result as the normal blood vessel. Upon receiving an operation of selecting the region 1513 displayed as the microbleeds by the cursor 1540 and pressing the "normal" button 1521, the display control unit 22 changes the mark 1531 representing the microbleeds attached to the region 1513 to the mark 1532 representing the normal blood vessel, and passes the information to the image processing unit 20B. The same applies to the change from the "normal blood vessel" to the "microbleeds".

Figure 16:
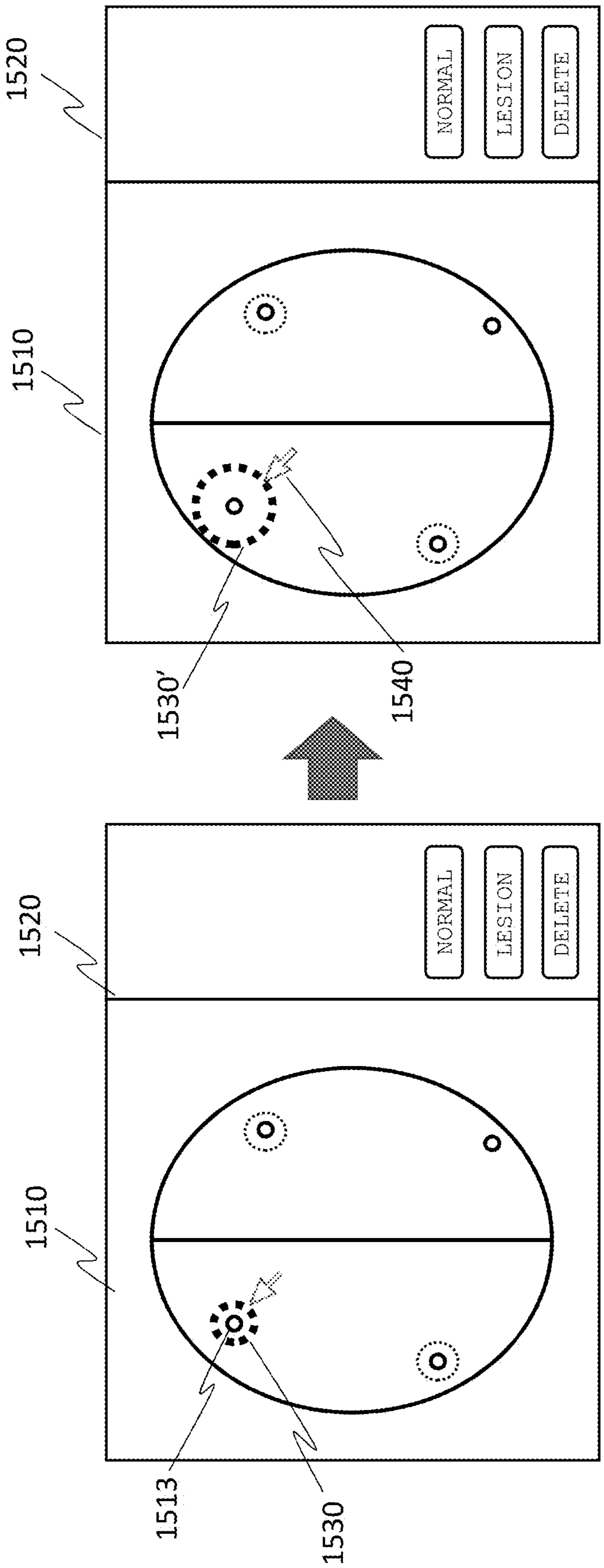
FIG. 16 illustrates a display example 4 of the display screen according to the third embodiment.

It is further possible to accept a modification in size, location, and so on, of the area to be marked, though not the modification of the discrimination result. In the example as shown in FIG. 16, the mark 1530 attached to the region 1513 displayed as the microbleeds is selected, and the size of the mark 1530 is changed (enlarged) by operating the cursor 1540 via the input device such as a mouse. In addition, it is also possible to accept area-filling or partial erasure by an eraser function, and this allows discrimination and edition that reflect the determination based on the experiences of the user such as the doctor and the examiner.

The image processing unit 20B receives the result of the user edition as described above, and updates the discrimination result. In addition, the image processing unit 20B (feature analyzer 253) may calculate statistic values for the region newly added. Furthermore, as a result of the deletion, when the statistic values (for example, the number of microbleeds) are changed, those statistic values may be rewritten.

When there is a change in the discrimination result due to the edition by the user, the result may be updated and registered in a device such as the storage device 30, and transferred to the PACS 50, for instance. These processes may be performed automatically by the image processing unit 20B or may be performed upon receiving an instruction from the user.

According to the present embodiment, it is possible to obtain a highly reliable discrimination result by adding the function of the user's edition to the processing of the image processing unit 20B. Such reliable discrimination result may also help diagnosis in similar cases, as well as improving the accuracy of the CNN by utilizing this reliable discrimination result for the CNN training and relearning.

What is claimed is:

1. A magnetic resonance imaging apparatus comprising a computer configured to:
- control the magnetic resonance imaging apparatus to perform magnetic resonance (MR) imaging according to imaging conditions set in an examination protocol, collect magnetic resonance signals corresponding to measurement data from the magnetic resonance imaging of an examination target and reconstruct an MR image including indicating, for each pixel in the image, brightness information;
- process the reconstructed image, including for each pixel of the image, a brightness value, and specify a designated region in the MR image generated by the magnetic resonance imaging;
- generate a probability map indicating, for each pixel of the designated region in the MR image generated by the magnetic resonance imaging, a presence probability that the pixel of the designated region exists in a specific organ or tissue of the examination target; and
- highlight the designated region based on shape information and spatial information of the designated region in the MR image generated by the magnetic resonance imaging, wherein the spatial information of the designated region in the MR image generated by the magnetic resonance imaging includes the probability map and a brightness distribution of the designated region, the brightness distribution indicating changes in brightness value within the designated region.

2. The magnetic resonance imaging apparatus according to claim 1, wherein the spatial information additionally includes a tissue distribution of the designated region in tissues of the examination target.

3. The magnetic resonance imaging apparatus according to claim 1, the computer being further configured to
- create as a candidate image, an image of only a predetermined shape based on the shape information of the designated region, and discriminate between the designated region and other regions,
- the designated region being discriminated based on the spatial information of the candidate image.

4. The magnetic resonance imaging apparatus according to claim 1, the computer being further configured to create segmentation images of the organ or the tissue of the examination target, wherein the probability of the designated region is calculated with respect to the segmentation images.

5. The magnetic resonance imaging apparatus according to claim 4, wherein an image of the examination target is a brain image, and the segmentation images include a brain parenchyma image and a cerebrospinal fluid image.

6. The magnetic resonance imaging apparatus according to claim 1, the computer being further configured to discriminate between the designated region and other tissue, a CNN (convolutional neural network) trained in advance with features of the images including the designated region and the surrounding region thereof being used to discriminate the designated region.

7. The magnetic resonance imaging apparatus according to claim 1, the computer being further configured to use a CNN (convolutional neural network), which was trained in advance with multiple images having different brightness distributions of a predetermined shape, to acquire the brightness distribution of the designated region.

8. The magnetic resonance imaging apparatus according to claim 7, the computer being further configured to select and apply one of multiple trained CNNs (convolutional neural networks), which were trained in advance each under multiple imaging conditions, in response to an imaging condition under which the image that is acquired is to be processed.

9. The magnetic resonance imaging apparatus according to claim 1, the computer being further configured to use a brightness gradient on an outline of the designated region, as the brightness distribution.

10. The magnetic resonance imaging apparatus according to claim 1, wherein the reconstructed image that is processed is a two-dimensional image.

11. The magnetic resonance imaging apparatus according to claim 1, wherein the image that is processed is at least one of a T2* weighted image and a susceptibility-weighted image.

12. The magnetic resonance imaging apparatus according to claim 1, the computer being further configured to display on a display device, a processing result of the highlighting, together with the image.

13. The magnetic resonance imaging apparatus according to claim 12, the computer being further configured to display a GUI configured to accept user's modification on the result displayed on the display device, and pass the contents modified via the GUI, to further processing.

14. A magnetic resonance imaging apparatus comprising a computer configured to:

collect magnetic resonance signals of an examination target and reconstruct an image;

process the reconstructed image, and specify a designated region in the image;

highlight the designated region based on shape information of the designated region and spatial information of the designated region;

generate a probability map indicating, for each pixel of the designated region, a presence probability that the pixel of the designated region exists in a specific organ or tissue of the examination target, the spatial information of the designated region including the probability map;

create as a candidate image, an image of only a predetermined shape based on the shape information of the designated region, and discriminate between the designated region and other regions, the designated region being discriminated based on the spatial information of the candidate image;

extract a first geometric feature of the designated region, and extract a second geometric feature different from the first geometric feature; and remove the second geometric feature from the first geometric feature, to create the candidate image.

15. The magnetic resonance imaging apparatus according to claim 14, wherein the designated region is a region of microbleeds, and the computer is further configured to extract a circular shape, and extract a linear shape.

* * * * *